United States Patent
Compton et al.

(10) Patent No.: US 8,668,821 B2
(45) Date of Patent: Mar. 11, 2014

(54) DETECTION OF PHENOLS

(71) Applicant: Isis Innovation Limited, Oxford (GB)

(72) Inventors: Richard Guy Compton, Oxford (GB); Craig Edward Banks, Stockport (GB)

(73) Assignee: Isis Innovation Limited, Oxford (GB)

( * ) Notice: Subject to any disclaimer, the term of this patent is extended or adjusted under 35 U.S.C. 154(b) by 0 days.

(21) Appl. No.: 13/716,942

(22) Filed: Dec. 17, 2012

(65) Prior Publication Data

US 2013/0098779 A1    Apr. 25, 2013

Related U.S. Application Data

(62) Division of application No. 11/922,265, filed as application No. PCT/GB2006/002219 on Jun. 16, 2006.

(30) Foreign Application Priority Data

Jun. 16, 2005  (GB) .................................. 0512282.5
Feb. 3, 2006   (GB) .................................. 0602203.2

(51) Int. Cl.
*G01N 27/28*   (2006.01)
*G01N 27/403*  (2006.01)
*G01N 27/416*  (2006.01)
*G01N 27/49*   (2006.01)
*G01N 27/30*   (2006.01)

(52) U.S. Cl.
USPC ........................................ 205/787; 205/788.5

(58) Field of Classification Search
CPC ................................................. G01N 27/3277
USPC ................................. 204/400, 787; 205/788.5
See application file for complete search history.

(56) References Cited

U.S. PATENT DOCUMENTS 6,511,592 B1    1/2003  Hill et al.
2004/0106190 A1  6/2004  Yang et al.

FOREIGN PATENT DOCUMENTS

EP              0170446 A1    2/1986
JP              05196601 A    8/1993
WO        WO 2004/062801 A    7/2004

OTHER PUBLICATIONS

Hawley et al. (J. Electroanal. Chem. 10:376-386).*
Hapiot et al. (J. Electroanal. Chem. 362:257-265).*
Mure, et al. (J. Am. Chem. Soc. 115:7117-7127).*

(Continued)

*Primary Examiner* — Luan Van
*Assistant Examiner* — Steven Rosenwald
(74) *Attorney, Agent, or Firm* — Vinson & Elkins LLP

(57) ABSTRACT

According to the present invention, phenols may be detected using an electrochemical sensor comprising a first compound, a working electrode and an electrolyte in contact with the working electrode, wherein the first compound operatively undergoes a redox reaction at the working electrode to form a second compound which operatively reacts in situ with the phenol, wherein said redox reaction has a detectable redox couple and wherein the sensor is adapted to determine the electrochemical response of the working electrode to the consumption of said second compound on reaction with the phenol. The phenol may be, for example, a cannabinoid or a catechin compound.

22 Claims, 10 Drawing Sheets

(56) References Cited

OTHER PUBLICATIONS

Corbett, "Application of Oxidative Coupling Reactions to the Assay of p-Phenylenediamines and Phenols," Analytical Chemistry 47:308-313, 1975.

Mure and Klinman, "Synthesis and Spectroscopic Characterization of Model Compounds for the Active Cofactor in Copper Amine Oxidases," J. Am. Chem. Soc. 115:7117-7127, 1993.

Imabayashi, et al., "Amperometric Biosensor for Polyphenol Based on Horseradish Peroxidase Immobilized on Gold Electrodes," Electroanalysis 13:408-412, 2001.

International Search Report from PCT/GB2006/002219, Nov. 8, 2006.

European Search Report from GB0512282.5, Aug. 18, 2005.

* cited by examiner

DETECTION OF PHENOLS

CROSS REFERENCE TO RELATED APPLICATIONS

The present application is divisional application of U.S. patent application Ser. No. 11/922,265, filed on Jul. 10, 2009, which is a National Stage Application under 35 U.S.C. §371 (c) of PCT Application Serial No. PCT/GB2006/002219, filed Jun. 16, 2006, which claims priority to Great Britain Patent Application Serial No. 0512282.5, filed Jun. 16, 2005, and Great Britain Patent Application Serial No. 0602203.2, filed Feb. 3, 2006, each of which are incorporated herein by reference in their entirety.

FIELD OF THE INVENTION

The present invention relates to methods and apparatus for the detection and quantitative determination of analytes, in particular phenols, phenolic compounds and phenol derivatives.

BACKGROUND TO THE INVENTION

The prevalence of driving while affected by *cannabis* is rising. It has been shown that drugs are detected commonly among those involved in motor vehicle accidents, various studies reporting that up to 25% of drivers involved in accidents tested positive for illicit drugs, with *cannabis* being the most common found, followed by benzodiazepines, cocaine, amphetamines and opioids. It is apparent that drugs, when taken in combination with alcohol, and multiple drugs, present an even greater risk; drug driving is a significant problem, both in terms of a general public health issue and as a specific concern for drug users.

The primary active component of *cannabis* is $\Delta^9$-tetrahydrocannabinol (THC), the structure of which is shown below:

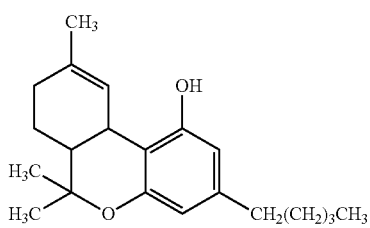

Studies have repeatedly shown that THC impairs cognition, psychomotor function and actual driving performance. For example, it has been reported that the degree of performance impairment observed in experimental studies after doses up to 300 μg per kg of THC were equivalent to the impairing effect of a blood alcohol concentration at the legal limit for driving under the influence in most European countries. The combined use of THC and alcohol produces severe impairment of cognitive, psychomotor, and actual driving performance and increases the risk of crashing.

Cannabinoids ($C_{21}$ compounds typical of and present in *cannabis*, their carboxylic acids, analogues, and transformation products) are routinely determined by gas chromatography-mass spectrometry (GC-MS). This approach requires complex instrumentation and all samples must be derivatized prior to injection. High-performance liquid chromatography, utilising electrochemical detection, has also been used. Low detection limits are achievable but high potentials are required for the electrochemical oxidation of cannabinoids. Typically, potentials of up to 1.2 V are required, which is close to the decomposition of water which increases the background current and introduces noise. Backofen et al (2000, BioMed. Chrom., 14:49) recently addressed this problem and explored non-aqueous electrolyte systems at platinum and gold electrodes, observing reduced noise and allowing a low detection limit of ca. 0.1 μM. This limit is two orders of magnitude lower than on-column UV detection and compares favourably with GC-MS.

As mentioned above, electrochemical methodologies have been employed as end of column detectors for THC. Typical sensing of THC is based on the oxidation of the hydroxyl group. This technique is not ideal since the electrochemical oxidation of phenols in aqueous solution is plagued by irreversible adsorption of oxidation reaction intermediates and products producing fouling of the electrode surface. This leads to poor electrode response and reproducibility, although this can be overcome to some extent by using low phenol concentrations and/or elevated temperatures. Alternative methods include the use of laser ablation to remove such passivating electrolytically generated layers or high overpotentials, which increase the anodic discharge of the solvent generating hydroxyl radicals which degrade the adsorbed oligomeric and polymeric products on the electrode surface.

A standard analytical technique for determining substituted phenol compounds is via reaction with the Gibbs reagent, i.e. 2,6-dichloro-p-benzoquinone 4-chloroimine. Gibbs showed that quinonechloroimides react with phenolic compounds producing brightly coloured indophenol compounds, which can be conveniently monitored via spectrophotometry. It was generally believed that the position para to the hydroxyl must be unsubstituted (Gibbs, (1927) J. Biol. Chem., 71:445; and Gibbs, (1927) J. Biol. Chem., 72:649). Gibbs reported that the pH of the solution greatly affects the rate of formation of the indophenol compound: at a pH of 10 the beginning of indophenol blue formation was observed to occur within two minutes, while at pH 8.5 this timescale was increased to 16 minutes. Dacre (1971, Anal Chem., 43:589) explored a large range of phenolic compounds and concluded that the Gibbs reaction was non-specific. A few substituted phenols were also reported as giving a negative Gibbs reaction.

Josephy and Damme (1984, Anal. Chem., 56:813) explored the Gibbs reaction with para-substituted phenols. The reaction mechanism is shown in Scheme 1 below:

Scheme 1

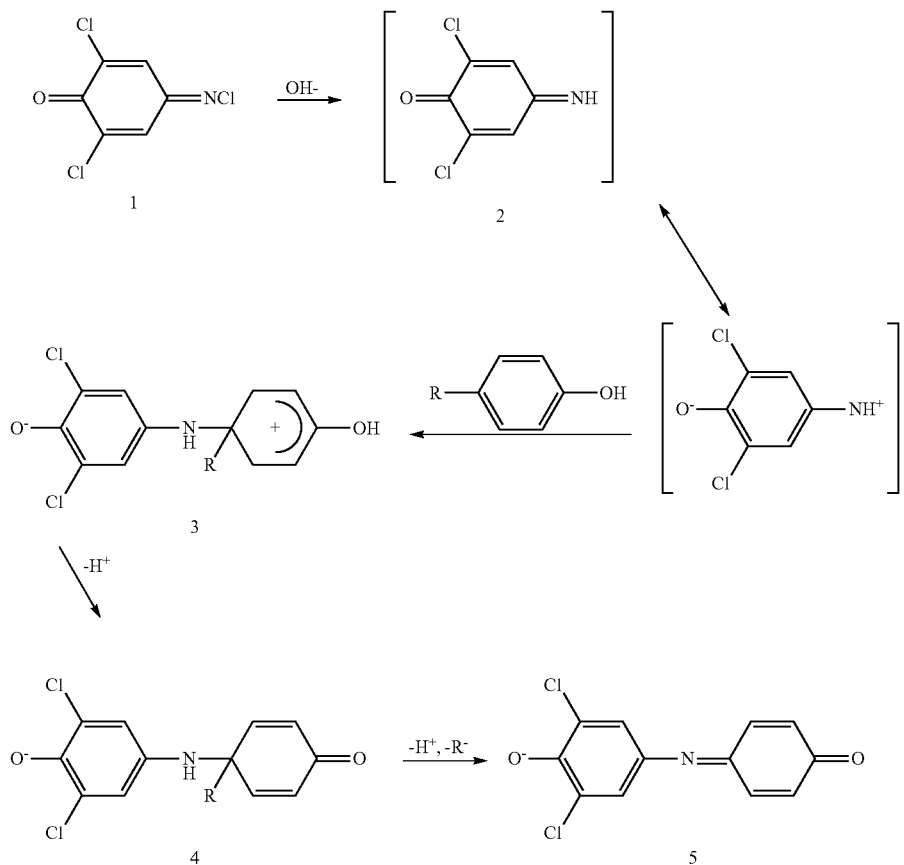

The mechanism involves first the solvolysis of the Gibbs reagent (1) which yields dichloro-benzoquinone monoamine (2). This attacks the para position of the phenol resulting in an adduct (4) which deprotonates with the resulting intermediate (4) losing a proton and R⁻, the para-substituted leaving group, to form 2,6-dichloroindophenol (5). Note that in the case R=H, (4) is oxidised to (5) by reaction with a second molecule of (2). The resulting indophenol is brightly coloured and can be easily characterised via spectrophotometry. However in their work, Josephy and Damme noted several exceptions which did not give a positive Gibbs reaction. These included halogen-substituted phenols (TCP, TBP and TIP), hydroxybenzaldehydes and related compounds, hydroxybenzyl alcohols and hydroxybenzoic acids. The reason why was not elucidated.

Green tea (*Camellia Sinensis*) is a rich source of polyphenol compounds known as catechins. Catechins are effective anti-cancer and anti-tumour agents and are claimed to have anti-mutagenic, anti-diabetic, hypocholesterolemic, anti-bacterial and anti-inflammatory properties. The most abundant catechins are (−)-epigallocatechin gallate (EGCG) and (−)-epigallocatechin (ECG) the structures of which are shown below:

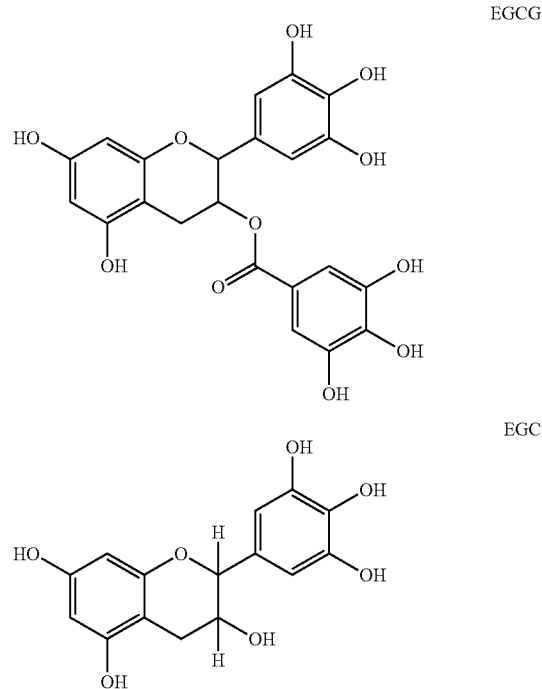

EGCG and EGC are thought to be the most effective catechin compounds, and the important characteristics of green tea, e.g. taste, nutritional values, palatability and pharmacological effects, depend substantially on their polyphenol content.

Methods of detecting catechins include high performance liquid chromatography using end of column detectors such as a coulometric array, UV, mass spectrometry and electrochemical detection. Caffeine, a major component in tea, can interfere with the UV analysis of catechins. Chromatographic methods coupled with electrochemical detection showed improved selectivity since caffeine is electrochemically inactive. Such a technique is based on simply holding an electrode at a suitably high potential which corresponds to the electrochemical oxidation of the analyte of interest. However, it is well documented that the electrochemical oxidation of phenolic compounds results in deactivation of the electrode surface (Pelillo et al, *Food Chem.* 87, (2004), 465; and Wang et al, *J. Electroanal. Chem.* 313, (1991), 129); a passivating polymeric film is produced which decreases the sensitivity and degrades the reproducibility although this can be overcome to a certain extent by using low phenol concentrations. The electrode materials employed in electrochemical end of column detectors include noble metals (Sano et al, *Analyst* 126, 2001, 816; and Yang et al, *Anal. BioChem.* 283, 2000, 77) and glassy carbon (Kumamoto et al, *Anal. Sci.*, 16, 2000, 139; and Long et al, *J. Chrom. B* 763, 2001, 47) electrodes. Recently, Romani et al (*J. Agric. Food Chem.* 48, 2000, 1197) explored screen-printed electrodes modified with tyrosinase enzyme as an electrochemical end of column sensor where the disposable aspect overcomes electrode fouling and alleviates the need to polish the electrode surface between runs.

In summary, the methods described above are limited by the complexity of instrumentation, a need to derivatize samples, unacceptable detection limits, high oxidation potentials or a lack of specificity.

SUMMARY OF THE INVENTION

The present invention modifies or builds on the known Gibbs reaction by electrochemically oxidising a p-aminophenol (PAP) to form a benzoquinone monoamine (for example, a dichloro- or diphenyl-benzoquinone monoamine), which then reacts with the substituted phenol compound of interest, as in the classical Gibbs reaction. Monitoring the reduction of an oxidised PAP provides an indirect method of detecting phenols and phenolic compounds, for example phenol, 4-phenoxyphenol, methylphenol (para and meta), nitrophenol, cannabinoids (e.g. tetrahydrocannabinol) and catechins (e.g. EGCG or ECG). The methodology according to the present invention is attractive since it avoids the direct oxidation of the phenol, which can lead to electrode passivation. The PAP may be present in the electrolyte and/or on the surface or in the bulk of the working electrode material.

According to a first aspect of the invention there is provided an electrochemical sensor for the detection of a phenol, which comprises a first compound, a working electrode and an electrolyte in contact with the working electrode, wherein the first compound operatively undergoes a redox reaction at the working electrode to form a second compound which operatively reacts in situ with the phenol, wherein said redox reaction has a detectable redox couple and wherein the sensor is adapted to determine the electrochemical response of the working electrode to the consumption of said second compound on reaction with the phenol.

According to a second aspect of the invention there is provided a method of sensing a phenol in a sample, comprising:
(a) oxidising a first compound at the working electrode of an electrochemical sensor to form a second compound which is operatively reactive with the phenol;
(b) contacting the phenol with the second compound in the presence of an electrolyte, such that the second compound reacts with the phenol; and
(c) determining the electrochemical response of the working electrode to the consumption of the second compound on reaction with the phenol.

According to a third aspect of the invention there is provided a method of forming an indophenol compound comprising electrochemically oxidising a 4-aminophenol compound to form a benzoquinone compound, and reacting the benzoquinone compound with a phenol to form an indophenol.

A further aspect of the invention is an electrode material comprising a 4-aminophenol compound. The material may be present on a surface and/or in the bulk of the electrode material.

DESCRIPTION OF VARIOUS EMBODIMENTS

Figure 1:
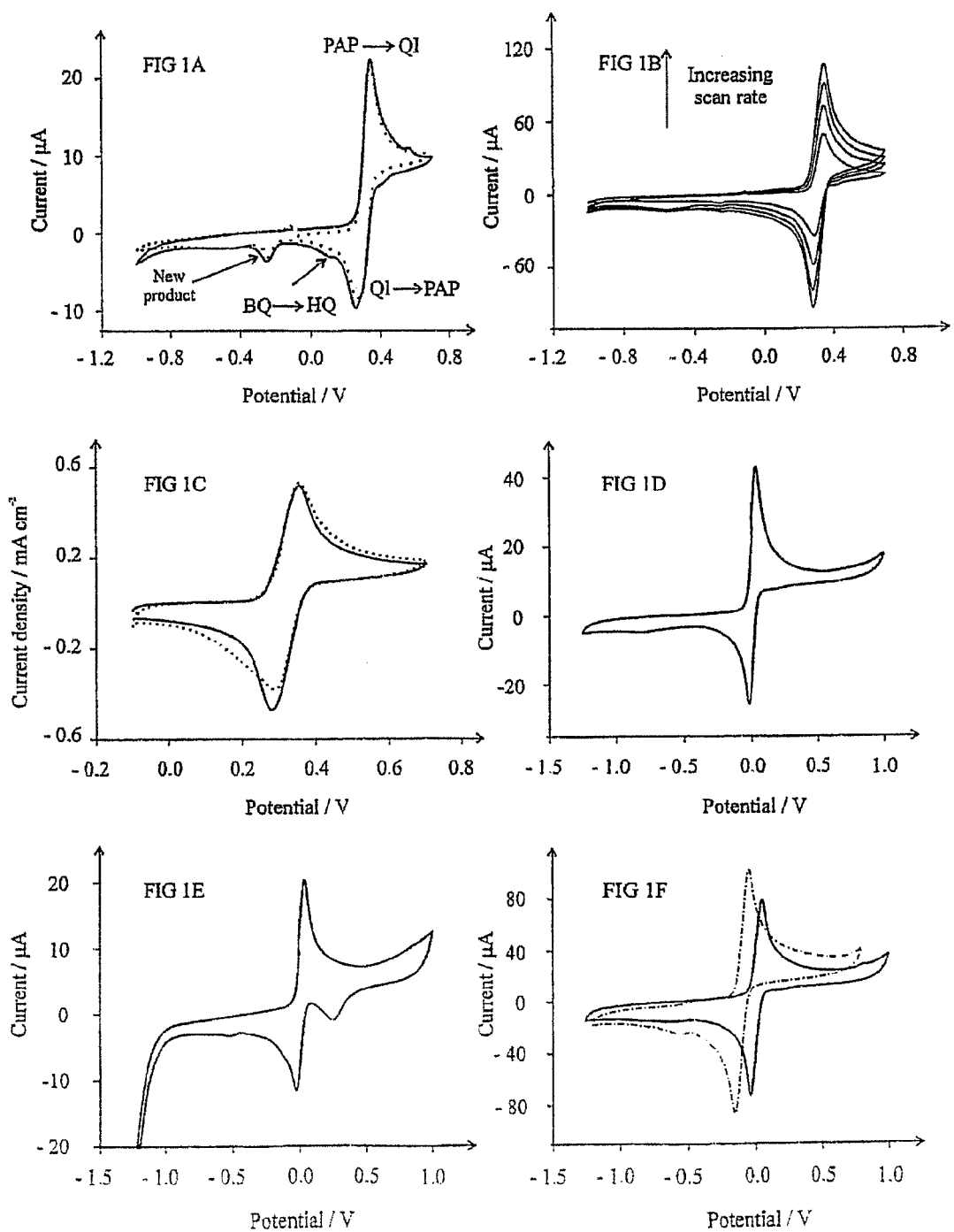
FIG. 1A shows the cyclic voltammogramic response to 1 mM 4-amino-2-,6-dichlorophenol at a scan rate of 5 mVs$^{-1}$ in pH 3.4 buffer.
FIG. 1B shows the scan rate dependence of 4-amino-2,6-dichlorophenol from 25 to 100 mVs$^{-1}$ in pH 3.4 buffer.
FIG. 1C compares the response of a gold macroelectrode (dotted line) to 4-amino-2,6-dichlorophenyl with that of an edge plane pyrolytic graphite (eppg) electrode at a scan rate of 100 mVs$^{-1}$ in pH 3.4 buffer.
FIGS. 1D and 1E compare the response of eppg and gold electrodes to 4-amino-2,6-dichlorophenyl recorded in a pH 10 buffer at 25 mVs$^{-1}$.
FIG. 1F shows the oxidation of 1 mM benzoquinone (BQ) to hydroquinone (HQ) at an eppg electrode in a pH 10 buffer (dotted line) compared with PAP at pH 10, both recorded at 100 mVs$^{-1}$.

The term "hydrocarbyl" as used herein includes reference to a moiety consisting exclusively of hydrogen and carbon atoms; such a moiety may comprise an aliphatic and/or an aromatic moiety. The moiety may comprise 1, 2, 3, 4, 5, 6, 7, 8, 9, 10, 11, 12, 13, 14, 15, 16, 17, 18, 19 or 20 carbon atoms. Examples of hydrocarbyl groups include $C_{1-6}$ alkyl (e.g. $C_1$, $C_2$, $C_3$ or $C_4$ alkyl, for example methyl, ethyl, propyl, isopropyl, n-butyl, sec-butyl or tert-butyl); $C_{1-6}$ alkyl substituted by aryl (e.g. phenyl) or by cycloalkyl; cycloalkyl (e.g. cyclopropyl, cyclobutyl, cyclopentyl or cyclohexyl); aryl (e.g. phenyl, naphthyl or fluorenyl) and the like.

The terms "alkyl" and "$C_{1-6}$ alkyl" as used herein include reference to a straight or branched chain alkyl moiety having 1, 2, 3, 4, 5 or 6 carbon atoms. This term includes reference to groups such as methyl, ethyl, propyl (n-propyl or isopropyl), butyl (n-butyl, sec-butyl or tert-butyl), pentyl, hexyl and the like.

The terms "alkenyl" and "$C_{2-6}$ alkenyl" as used herein include reference to a straight or branched chain alkyl moiety having 2, 3, 4, 5 or 6 carbon atoms and having, in addition, at least one double bond, of either E or Z stereochemistry where applicable. This term includes reference to groups such as ethenyl, 2-propenyl, 1-butenyl, 2-butenyl, 3-butenyl, 1-pentenyl, 2-pentenyl, 3-pentenyl, 1-hexenyl, 2-hexenyl and 3-hexenyl and the like.

The terms "alkynyl" and "$C_{2-6}$ alkynyl" as used herein include reference to a straight or branched chain alkyl moiety having 2, 3, 4, 5 or 6 carbon atoms and having, in addition, at least one triple bond. This term includes reference to groups such as ethynyl, 1-propynyl, 2-propynyl, 1-butynyl, 2-butynyl, 3-butynyl, 1-pentynyl, 2-pentynyl, 3-pentynyl, 1-hexynyl, 2-hexynyl and 3-hexynyl and the like.

The terms "alkoxy" and "$C_{1-6}$ alkoxy" as used herein refer to —O-alkyl, wherein alkyl is straight or branched chain and comprises 1, 2, 3, 4, 5 or 6 carbon atoms. In one class of embodiments, alkoxy has 1, 2, 3 or 4 carbon atoms. This term includes reference to groups such as methoxy, ethoxy, propoxy, isopropoxy, butoxy, tert-butoxy, pentoxy, hexoxy and the like.

The term "cycloalkyl" as used herein includes reference to an alicyclic moiety having 3, 4, 5, 6, 7 or 8 carbon atoms. The group may be a bridged or polycyclic ring system. More often cycloalkyl groups are monocyclic. This term includes reference to groups such as cyclopropyl, cyclobutyl, cyclopentyl, cyclohexyl, norbornyl, bicyclo[2.2.2]octyl and the like.

The term "aryl" as used herein includes reference to an aromatic ring system comprising 6, 7, 8, 9, 10, 11, 12, 13, 14, 15 or 16 ring carbon atoms. The group is often phenyl but may be a polycyclic ring system, having two or more rings, at least one of which is aromatic. This term includes reference to groups such as phenyl, naphthyl, fluorenyl, azulenyl, indenyl, anthryl and the like.

The term "carbocyclyl" as used herein includes reference to a saturated (e.g. cycloalkyl or cycloalkenyl) or unsaturated (e.g. aryl) ring moiety having 3, 4, 5, 6, 7, 8, 9, 10, 11, 12, 13, 14, 15 or 16 carbon ring atoms. A carbocyclic moiety is, for example, selected from cyclopropyl, cyclobutyl, cyclopentyl, cyclohexyl, norbornyl, bicyclo[2.2.2]octyl, phenyl, naphthyl, fluorenyl, azulenyl, indenyl, anthryl and the like.

The term "heterocyclyl" as used herein includes reference to a saturated (e.g. heterocycloalkyl) or unsaturated (e.g. heteroaryl) heterocyclic ring moiety having from 3, 4, 5, 6, 7, 8, 9, 10, 11, 12, 13, 14, 15 or 16 ring atoms, at least one of which is selected from nitrogen, oxygen, phosphorus and sulphur. A heterocyclic moiety is, for example, selected from thienyl, furanyl, tetrahydrofuryl, pyranyl, thiopyranyl, benzofuranyl, pyrrolyl, pyrrolinyl, pyrrolidinyl, imidazolyl, imidazolidinyl, benzimidazolyl, pyrazolyl, pyrazinyl and the like.

The term "heterocycloalkyl" as used herein includes reference to a saturated heterocyclic moiety having 3, 4, 5, 6 or 7 ring carbon atoms and 1, 2, 3, 4 or 5 ring heteroatoms selected from nitrogen, oxygen, phosphorus and sulphur. The group may be a polycyclic ring system but more often is monocyclic. This term includes reference to groups such as azetidinyl, pyrrolidinyl, tetrahydrofuranyl, piperidinyl, oxiranyl, pyrazolidinyl, imidazolyl, indolizidinyl, piperazinyl, thiazolidinyl, morpholinyl, thiomorpholinyl, quinolizidinyl and the like.

The term "heteroaryl" as used herein includes reference to an aromatic ring system having 5, 6, 7, 8, 9, 10, 11, 12, 13, 14, 15 or 16 ring atoms, at least one of which is selected from nitrogen, oxygen and sulphur. The group may be a polycyclic ring system, having two or more rings, at least one of which is aromatic, but is more often monocyclic. This term includes reference to groups such as pyrimidinyl, furanyl, benzo[b]thiophenyl, thiophenyl, pyrrolyl, imidazolyl, pyrrolidinyl, pyridinyl, benzo[b]furanyl, pyrazinyl, indolyl, benzimidazolyl, quinolinyl, phenothiazinyl, triazinyl, oxazolyl, isoxazolyl, thiazolyl, isoindolyl, indazolyl, isoquinolinyl, quinazolinyl and the like.

The term "halogen" as used herein includes reference to F, Cl, Br or I.

Typically, electrochemical sensors are based upon the configuration of an electrochemical cell, with an electrolyte and at least two electrodes, for example. In potentiometric measurements, there is no current passing through the cell, and these two electrodes are sufficient. A signal is measured as the potential difference (voltage) between the two electrodes.

Amperometric sensors are a type of electrochemical sensor, in which measurements are made by monitoring the current in the electrochemical cell between a working electrode (also called a sensing electrode) and a counter electrode (also called an auxiliary electrode) at a certain potential (voltage). These two electrodes are separated by an electrolyte. A current is produced when the sensor is exposed to a medium containing an analyte because the analyte reacts within the sensor, either producing or consuming electrons (e$^-$). That is, the analyte is oxidized or reduced at the working electrode. The oxidation or reduction of the analyte will cause a change in current between the working and counter electrodes, which will be related to the concentration of the analyte. Complementary chemical reactions will occur at each of the working electrode and counter electrode. In suitable applications, these reactions can be accelerated by an electrocatalyst, such as a platinum electrode or another material on the surface of the electrodes, or there can be a sacrificial electrode process in which the electrode material is consumed, for example with Ag/AgCl electrodes. For amperometric sensors, in a cyclic voltammetry experiment, an external potential is applied to the cell, and the current response is measured. Precise control of the external applied potential is required, but this is generally not possible with a two-electrode system, due to the potential drop across the cell due to the solution resistance and the polarization of the counter electrode that is required to complete the current measuring circuit. Better potential control is achieved using a potentiostat and a three-electrode system, in which the potential of one electrode (the working electrode) is controlled relative to the reference electrode, and the current passes between the working electrode and the third electrode (the counter electrode).

The choice of suitable sensor arrangement and materials is important when considering the moiety to be sensed, temperature range and electrochemical method to be used. Amperometric sensors have been found to enable low cost of components, small size, and lower power consumption than other types of sensor, and are ideal for use in portable analysis systems. In the present invention, amperometric sensing methodology is typically employed.

In the present invention, phenols are generally detected indirectly. In particular, the present invention involves the use of a compound which operatively undergoes a redox reaction at the working electrode, wherein the reaction has a detectable redox couple and wherein the product of said reaction operatively reacts in situ with the phenol. The electrochemical response of the working electrode to the consumption of the said compound on reaction with the phenol is then determined. The phenol may be contacted with the compound prior to, contemporaneously with or subsequent to the oxidation of the compound, but is typically admitted subsequent thereto.

The term "phenol" as used herein includes reference to phenols, phenolic compounds and derivatives thereof.

The phenol may be, for example, phenol, 4-phenoxyphenol, p-methylphenol, m-methylphenol, nitrophenol, tetrahydrocannabinol, a component or metabolite of *cannabis*, a natural or synthetic cannabinoid or metabolite thereof, or a catechin such as EGCG or EGC. An example of a *cannabis* or cannabinoid metabolite is a metabolite found in urine, and especially 11-nor-9-carboxy-9-tetrahydrocannabinol. The phenol is preferably para-substituted.

The first compound may be a 4-aminophenol (or p-aminophenol). In one embodiment, the first compound is a compound of the formula (I):

(I)

wherein
  m is 0, 1, 2, 3 or 4;
  each $R^1$ is independently $R^2$, or is hydrocarbyl or heterocyclyl, either of which is optionally substituted with 1, 2, 3, 4 or 5 $R^2$;
  each $R^2$ is independently selected from halogen, trifluoromethyl, cyano, nitro, oxo, $=NR^3$, $R^3$, $-OR^3$, $-C(O)R^3$, $-C(O)OR^3$, $-OC(O)R^3$, $-N(R^3)R^4$, $-C(O)N(R^3)R^4$, $-S(O)_lR^3$ and $-C(R^3)_3$;
  $R^3$ and $R^4$ are each independently hydrogen, or are selected from $C_{1-6}$ alkyl, $-(CH_2)_k$-carbocyclyl and $-(CH_2)_k$-heterocyclyl, any of which is optionally substituted with 1, 2, 3, 4 or 5 substituents independently selected from halogen, hydroxy and $C_{1-6}$ alkyl; and
  l is 0, 1 or 2.

A compound of formula (I) is generally oxidised at the working electrode to form a compound of formula (II):

(II)

In one embodiment, m is 0. In another embodiment, m is at least 1 (e.g. 1 or 2).

$R^1$ may be hydrocarbyl, for example $C_{1-6}$ alkyl (e.g. methyl, ethyl, propyl, isopropyl, n-butyl, sec-butyl or tert-butyl), $C_{1-6}$ alkyl substituted by aryl (e.g. benzyl), cycloalkyl (e.g. cyclopropyl, cyclobutyl, cyclopentyl or cyclohexyl) and aryl (e.g. phenyl, naphthyl or fluorenyl), any of which may be substituted with 1, 2, 3, 4 or 5 $R^2$.

Alternatively, $R^1$ may be heterocyclyl, for example heterocycloalkyl (e.g. tetrahydrofuranyl) and heteroaryl (e.g. furanyl, pyranyl, thiophenyl, benzothiophenyl), either of which may be substituted with 1, 2, 3, 4 or 5 $R^2$.

In another class of compounds, each $R^1$ is $C_{1-6}$ alkyl (e.g. methyl, ethyl, propyl, isopropyl, n-butyl, sec-butyl or tert-butyl) or $C_{1-6}$ alkoxy (e.g. methoxy or ethoxy), either of which is optionally substituted with, for example, halogen or hydroxyl.

In a further class of compounds, each $R^1$ is carbocyclyl, for example aryl, optionally substituted with 1, 2, 3, 4 or 5 $R^2$. In particular, each R may be phenyl optionally substituted 1, 2, 3, 4 or 5 $R^2$.

$R^1$ may be $R^2$, in which case $R^2$ is typically selected from halogen (e.g. chlorine), hydroxy, cyano, nitro, oxo, carboxy, amino, alkylamino, dialkylamino and $C_{1-6}$ alkyl (e.g. methyl or ethyl).

In certain compounds, each $R^1$ is independently selected from —$NR^3R^4$, halogen, $C_1$, $C_2$, $C_3$ or $C_4$ alkyl, $C_1$, $C_2$, $C_3$ or $C_4$ haloalkyl, $C_1$, $C_2$, $C_3$ or $C_4$ alkoxy, and $C_2$, $C_3$ or $C_4$ alkenyl, wherein $R^3$ and $R^4$ are each independently selected from hydrogen, —OH, $C_1$, $C_2$, $C_3$ or $C_4$ alkyl, $C_1$, $C_2$, $C_3$ or $C_4$ haloalkyl, $C_1$, $C_2$, $C_3$ or $C_4$ alkoxy, and $C_2$, $C_3$ or $C_4$ alkenyl.

In one class of compounds, each $R^1$ is halogen, in particular chlorine.

In a particular embodiment, the compound of formula (I) is a compound of formula (IA) or (IB):

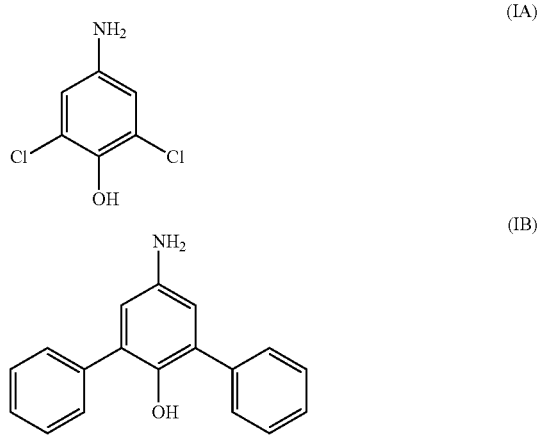

The first compound may be present in the electrolyte and/or on the working electrode and/or in the working electrode. In a particular embodiment, the electrolyte comprises the first compound. A working electrode comprising the first compound may be obtained by immobilising the compound on the electrode from solution, using a compound having a low solubility in the solvent. Solubility of the compound may be optimised by controlling its molecular weight. By way of example, 2,6-diphenyl-4-amino-phenol can be immobilised on an electrode substrate from a solvent such as acetonitrile. Alternatively, the first compound may be comprised in the bulk of the electrode material.

The working electrode may be a screen printed electrode, a metallic electrode, an edge plane pyrolytic graphite electrode, a basal plane pyrolytic graphite electrode, a gold electrode, a glassy carbon electrode, a boron doped diamond electrode, or a highly ordered pyrolytic graphite electrode. The working electrode may be a microelectrode or a macroelectrode.

Determination of the electrochemical response of the working electrode may comprise measuring the current flow between the working electrode and a counter electrode to determine the amount of the phenol or phenolic compound. It is particularly preferred that the working electrode is operatively maintained at a constant voltage.

In one embodiment, the current is measured using linear sweep or cyclic voltammetry. In another embodiment, said current is measured using square wave voltammetry. In an alternative embodiment, the current is measured using a pulsed voltammetry technique, in particular differential pulse voltammetry.

The following Examples illustrate the invention.

Materials and Methods

All chemicals were of analytical grade and used as received without any further purification. These were $\Delta^9$-tetrahydrocannabinol (HPLC grade, >90%, ethanol solution), 2,6-dichloro-p-aminophenol, phenol, 4-phenoxyphenol, methylphenol (para and meta), nitrophenol, 4-amino-2,6-dichlorophenol (>98% Sigma-Aldrich), epigallocatechin gallate (minimum 97%, Sigma-Aldrich), epigallocatechin (minimum 98%, HPLC grade, Sigma-Aldrich) and 4-amino-2,6-diphenylphenol (>98%, Sigma-Aldrich). The green tea leaf sample (Xiamen Tea IMP, & EXP. CO., LTD) was purchased from a local Chinese supermarket.

Solutions were prepared with deionised water of resistivity not less than 18.2 M Ohm cm (Millipore Water Systems). Voltammetric measurements were carried out using a µ-Autolab II potentiostat (Eco-Chemie) with a three-electrode configuration. Edge and basal plane pyrolytic graphite electrodes (Le Carbone Ltd.) were used as working electrodes. In the former case, discs of pyrolytic graphite were machined into a 4.9 mm diameter, which was oriented with the disc face parallel with the edge plane, or basal plane as required. The basal plane pyrolytic graphite electrode was prepared by renewing the electrode surface with cellotape. This procedure involves polishing the bppg electrode surface on carborundum paper (P100 grade) and then pressing cellotape on the cleaned bppg surface which is removed along with attached graphite layers. This was then repeated several times. The electrode was then cleaned in water and acetone to remove any adhesive. The counter electrode was a bright platinum wire, with a saturated calomel electrode completing the circuit. The EPPG electrodes were polished on alumina lapping compounds (BDH) of decreasing sizes (0.1 to 5 µm) on soft lapping pads.

All experiments were typically conducted at 20±2° C. Before commencing experiments, nitrogen (BOC) was used for deaeration of solutions. Stock solutions of the substituted phenols were prepared by dissolving the required substituted phenol in ethanol.

Initial Voltammetric Characterisation of 4-amino-2,6-dichlorophenol (PAP)

First, the voltammetric response of an eppg electrode in pH 3.4 buffer solution containing 1 mM 4-amino-2,6-dichlorophenol (PAP) was explored. The corresponding voltammetry is shown in FIG. 1A. The first cyclic (dotted line) shows an oxidation peak at ca.+0.36 V (vs. standard calomel electrode;

SCE) with a corresponding reduction peak at ca.+0.24V (vs. SCE) which is due to the redox system of p-aminophenol-quinoneimine (PAP-QI), i.e.:

$$H_2N—C_6H_2Cl_2OH-2H^+-2e \rightleftharpoons HN=C_6H_2Cl_2=O$$

or, equivalently:

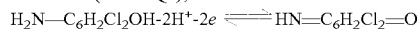
Scheme 2

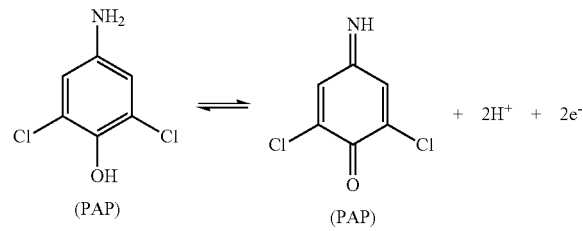

The reduction wave is smaller than the corresponding oxidation peak, which is due to an electrochemical mechanism occurring in which the quinoneimine (QI) is slowly hydrolysed to form a benzoquinone (BQ):

Scheme 3

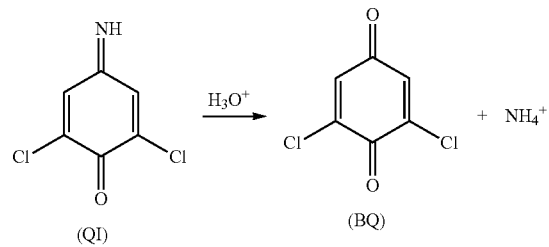

This mechanism has been previously studied on platinum and mercury electrodes. A small peak is observed on the cathodic scan at ca.+0.06 V, (see FIG. 1A) which is due to the reduction of BQ to hydroquinone (HQ) (Hawley et al, 1965, J. Electroanal. Chem., 10:376). At ca.−0.27V (vs. SCE) a new wave appears; it has been shown that this is due to the benzoquinone rapidly reacting with PAP via 1,4-addition reactions, with the main product being 2,5-bis(4-hydroxyanilino)-p-benzoquinone. On the second voltammetric scan, (FIG. 1A), some new 'bumps' have appeared on the voltammogram, which is likely due to the fouling of the electrode. These, and the new waves occurring from the electrochemical mechanism are well resolved from the main redox features of the voltammogram, indicating that the PAP-QI redox couple may be used as a marker from which to monitor the loss of QI as it reacts with phenols, phenolic compounds and phenol derivatives.

Next the variation of the peak potential with pH was explored. The cathodic and anodic waves were observed to shift toward more negative potentials from increasing the pH. A plot of formal potential against pH was observed to be linear from pH 0.84 to pH 7 with the gradient found to be 61 mV per unit (Ep=0.061 pH+0.57; R2=0.998) which suggests an n-electron, n-proton process where n is likely to be 2. Beyond pH 7 the plot of peak potential vs. pH was non-linear which is attributed to a pKa of 7.3 (calculated using ACD/Labs Sloaris V4.67 software) and is in agreement with previous studies (Hawley et al, 1965, J. Electroanal. Chem., 10:376; Salavagione et al, 2004, J. Electroanal. Chem., 565: 375; and Bramwell et al, 1990, Analyst, 115:185).

Cyclic voltammograms were recorded over a range of scan rates as shown in FIG. 1B, with analysis of the peak height (oxidation) versus square root of scan rate revealing a linear dependence indicating a diffusing species. From this plot the diffusion coefficient of 2,6-dichloro-p-aminophenol was estimated to be 4.4 ($\pm$0.3)$\times 10^{-6}$ cm s$^{-1}$ (in pH 3.4 phosphate buffer) for n=2, which is in agreement with 4.8$\times 10^{-6}$ cm s$^{-1}$ reported for 2,6-dichloro-p-aminophenol in 2 M sulphuric acid (Adams, 1969, Electrochemistry at Solid Electrodes, Marcel Dekker, New York).

The response of a gold macroelectrode was next sought so as to compare with that of the edge plane pyrolytic graphite electrode at the same pH; the results are shown in FIG. 1C. Equivalent responses are observed on the gold substrate and an eppg electrode. Also similar peak-to-peak separations are observed: 78 mV (at 100 mVs$^{-1}$) at the gold and 85 mV (at 100 mVs$^{-1}$) at the eppg electrode. Both these results indicate quasi-reversible electrode kinetics on each substrate.

From the literature a range of pH values has been recommended as suitable for carrying out the Gibbs reaction. Gibbs (1927, J. Biol. Chem. 72:649), Baylis (1928, J. Am. Water Works Assoc., 19:597), Ruchhoft (1948, Anal. Chem., 20:1191) and Theriault (1929, Ind. Eng. Chem., 21:343) suggested pH values of 9.1 to 9.5, 9.6 to 10, 9 to 10 and 9.4 respectively. It therefore appears that a pH range of from 9 to 10 is optimised for rapid completion of the Gibbs reaction. This is due to the required hydrolysis of the Gibbs reagent (species 1 of Scheme 1) to yield the dichloro-benzoquinone monoamine (species 2 of Scheme 1) which then undergoes the Gibbs reaction by attacking the substituted phenol. However, in the present invention this not need be a pre-requisite since the dichloro-benzoquinone monoamine is electrochemically generated and then reacts with the target compound. This means, usually providing that the voltammetry is well-resolved, that a method of the present invention is applicable over a range of pH values. Above, acidic conditions have been considered; an exploration the oxidation of the PAP at pH 10 at both eppg and gold electrodes follows.

In pH 10 the electrochemical oxidation wave of the PAP, as shown in FIG. 1D, has shifted to ca.+0.059 V (vs. SCE) at the eppg, having an identical voltammetric profile to that observed at pH 3.4, while the oxidation wave is observed at ca.+0.064 V on the gold electrode (FIG. 1E) is similar except with a new voltammetric reduction peak at ca.+0.23 V. This is likely to be due to electrode filming and close inspection of FIG. 1A reveals this is also observed on the eppg electrode although to a much lesser extent. Given the similar voltammetric response and inherent low cost of eppg electrodes compared with that of the gold and other electrode substrates, the use of eppg is considered to be particularly desirable and eppg electrodes are used throughout in the following Examples.

EXAMPLE 1

Detection of Phenol

The electrochemical adaptation of the Gibbs reaction for the detection of substituted phenols underlies the present invention and is discussed in more detail below. A pH 10 buffer solution containing 1 mM PAP was prepared and using a polished basal plane pyrolytic graphite electrode the initial cyclic voltammetric response was obtained. Note that either a polished bppg or an eppg electrode may be used since the edge plane sites are responsible for fast heterogeneous electron transfer kinetics and polishing of the bppg electrode leads to the formation of significant amounts of edge plane defects. Additions of phenol were made over the range of 50 to 250 μM to the solution with the observed response depicted in FIG. 2. Three important features are evident: the first is that the reduction peak at ca.−0.06 V has decreased with increasing phenol additions; second, the oxidation peak at ca.+0.05 V has decreased with phenol additions; and thirdly there is a new oxidation wave at ca.+0.46 V which slightly shifts in potential and grows with each addition of phenol.

Figure 2:
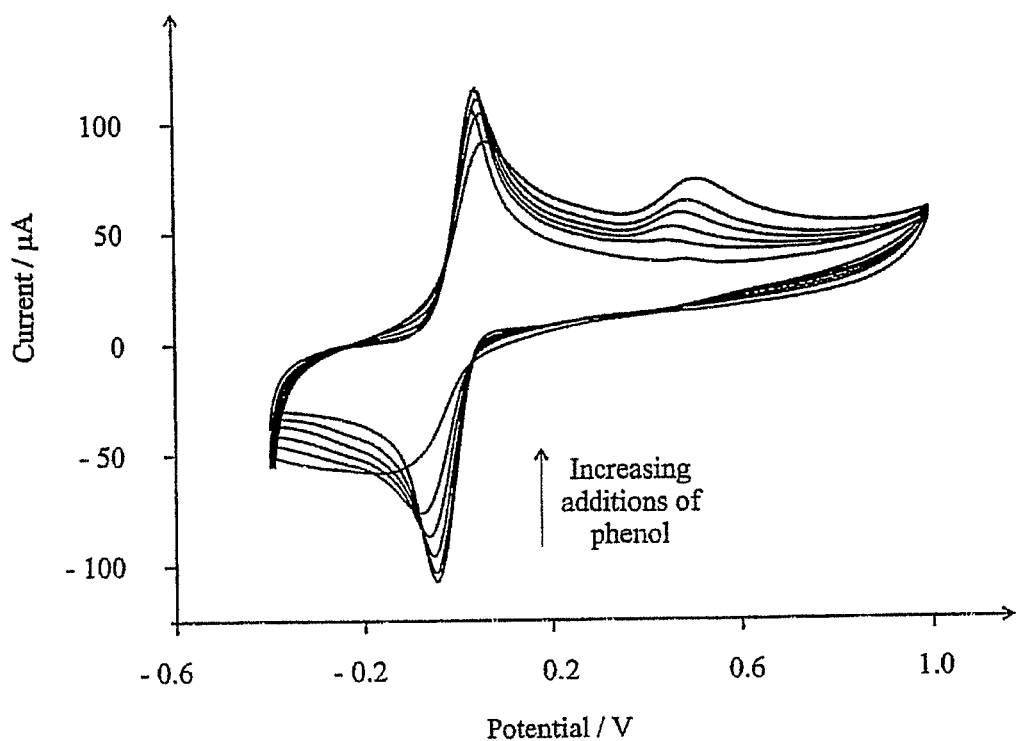
FIG. 2 shows cyclic voltammograms showing the response of phenol additions to a pH 10 buffer solution containing 1 mM 4-amino-2,6-dichlorophenol, using a polished basal plane pyrolytic graphite (bppg) electrode at a scan rate of 100 mVs$^{-1}$. The phenol additions were at 50, 100, 150, 200 and 250 μM.
Figure 3:
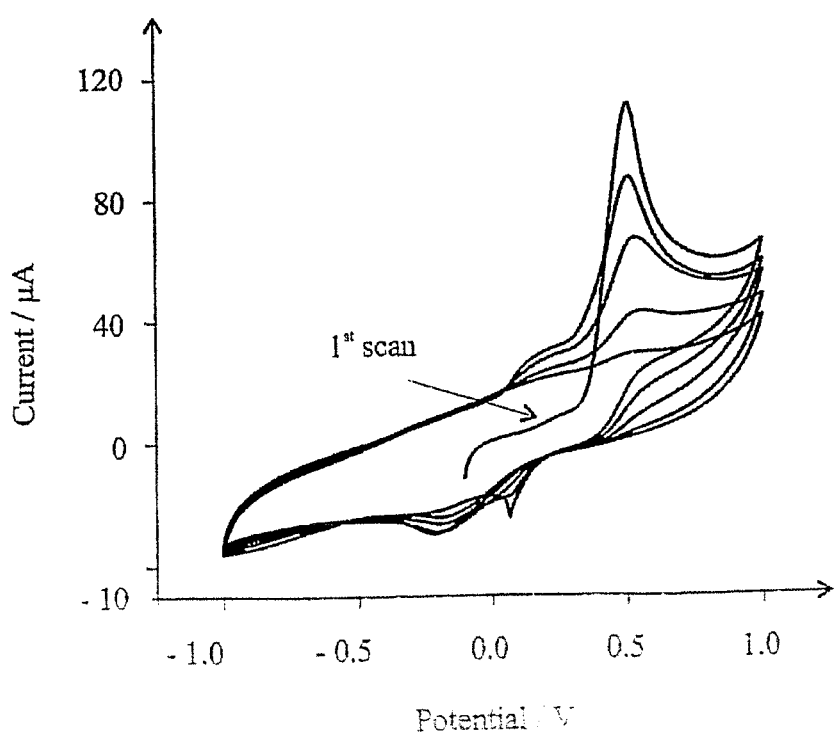
FIG. 3 is a voltammogram showing the oxidation of 1 mM phenol in a pH 10 buffer solution recorded at 100 mVs$^{-1}$ using an eppg electrode.

The new peak at ca.+0.46 V was explored by examining the voltammetry of 1 mM phenol in a pH 10 buffer solution. FIG. 3 shows that an oxidation wave is observed at ca.+0.5 V corresponding to the electrochemical oxidation of phenol. On successive scans, the peak diminishes. After the first scan, the background current has increased which indicates that probably electrode passivation has occurred. It is also likely that the new wave observed in FIG. 2 is a combination of the direct oxidation of phenol and/or polymeric species from the oxidation of aminophenol. In either case this feature is well resolved from the PAP-QI redox couple. Returning to FIG. 2, the analysis of the decreasing peak height ($I_H$) at ca.−0.06 V versus added phenol concentrations produced the following linear regression data: $I_H$=−0.19 [(phenol/M)]+1.12×10$^{-4}$; $R^2$=0.98, N=5. This suggests that the diminishing reduction wave can provide a simple analytical methodology for the indirect detection of phenol and phenolic compounds.

The response of PAP to increasing additions of phenol using square-wave voltammetry (SWV) at an edge plane pyrolytic graphite electrode was then explored, with a view to increasing the sensitivity of the protocol. SWV was used because this technique has an increased sensitivity over linear sweep (or cyclic voltammetry) due to the fact that the former is a measure of the net current, which is the difference between the forward and reverse current pulses. Also, using SWV, only one peak is observed allowing one to easily monitor the reduction of the voltammetry peak on additions of the phenol compound. First, however, the square-wave parameters were optimised. Using a pH 10 buffer solution containing 1 mM PAP, the frequency and step potential were each in turn changed to find the optimum peak height. This was found to occur when the frequency was 8 Hz, the step potential 10 mV and the amplitude 25 mV.

Figure 4:
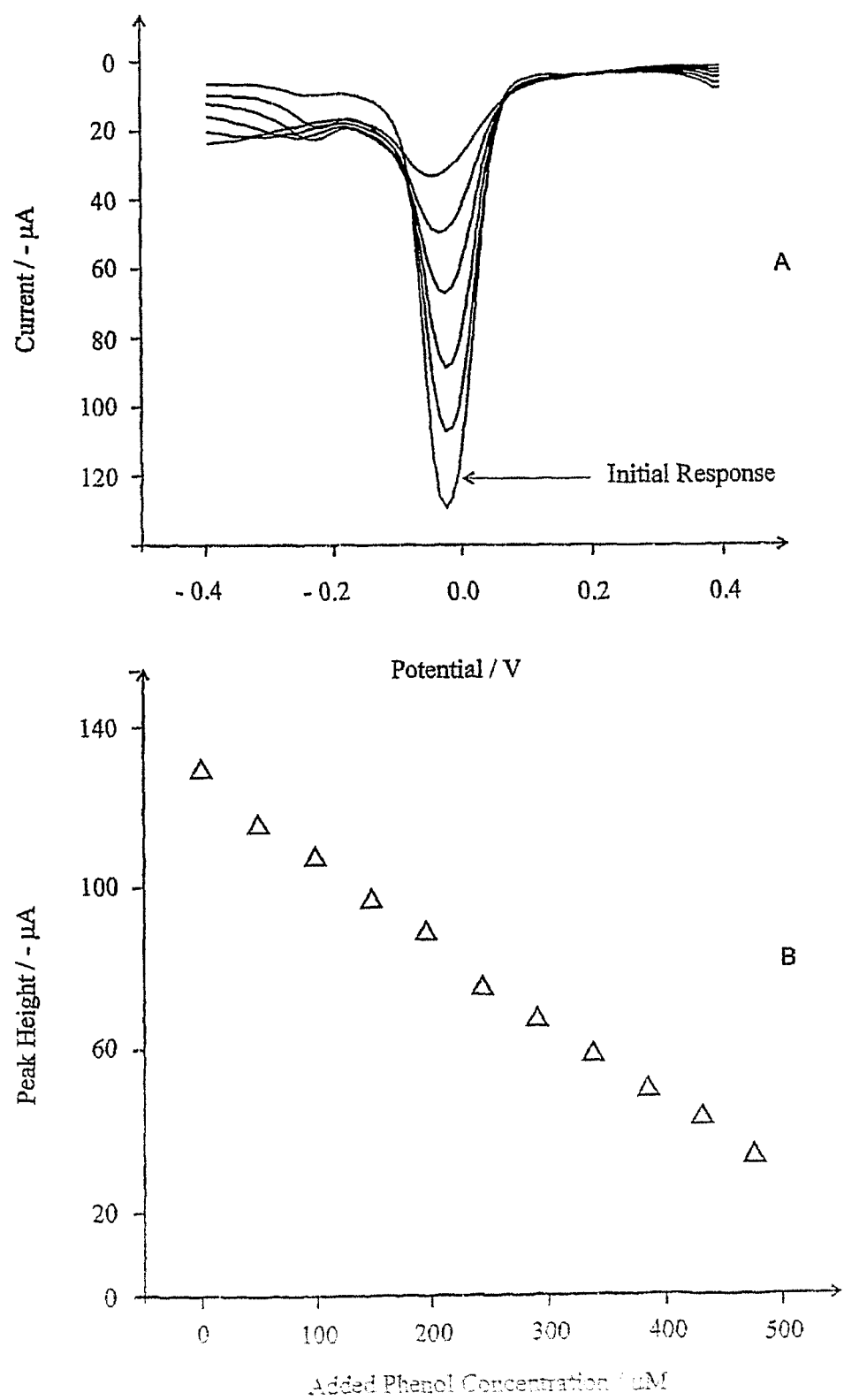
FIG. 4A shows square wave voltammograms of phenol additions to a 1 mM solution of PAP using an eppg electrode. The voltammetric response is for additions of phenols at 99, 196, 291, 385 and 485 μM respectively. The square wave parameters are: 10 s at +0.4V followed by a potential sweep from +0.4V to −0.4V.
FIG. 4B is a graph of the peak height versus added phenol concentration for voltammogram of FIG. 4A.

Using these parameters the square-wave voltammetric response from an eppg electrode was sought in a pH 10 buffer solution containing 1 mM PAP. The voltammogram was cycled until the peak had stabilised—which is typically after two cycles—after which phenol additions were made to the solution. As depicted in FIG. 4A, the well-defined voltammetric response was found to decrease with added phenol concentrations. Analysis of the peak current versus added phenol concentration was found to be highly linear from 50 to 480 μM ($I_H$=−0.198 [(phenol/M)]+1.26×10$^{-4}$; $R^2$=0.997, N=10) which is also shown in FIG. 4B. From this a limit of detection (3σ) was found to be 15.3 μM. Given the simplicity of the SWV technique this was used throughout the following.

Characterisation of the wave at ca.−0.2 V (FIG. 4A) was investigated by exploring the voltammetry of hydroquinone in a pH 10 buffer solution. Using an eppg electrode, a well-defined redox couple was observed, corresponding to the oxidation of HQ to BQ as depicted in FIG. 1F. For clarity the voltammetric response of the oxidation of PAP in pH 10 buffer at an eppg is overlaid. This also helps 'fingerprint' the new voltammetric features found when PAP is oxidised in aqueous solution, according to the mechanism shown in Scheme 2. Overall this demonstrates that the small voltammetric wave at ca.−0.2 V in FIG. 4A is due to the reduction of benzoquinone to hydroquinone formed via the hydrolysis of oxidised PAP as described above.

The initial concentration of PAP was explored to see if it was possible to extend the linear range of the phenol analysis or increase the sensitivity of the technique. The above experiment was repeated but with the concentration of PAP lowered to 0.1 mM with phenol additions made to the solution over the same linear range. Linear regression from analysis of the peak height versus added phenol concentration ($I_H$=−0.036 [(phenol/M)]+2.82×10$^{-5}$ 10; $R^2$=0.987, N=10) revealed that the sensitivity (gradient) was lower than that observed using a initial 1 mM concentration of PAP. Conversely using an initial 10 mM concentration of PAP, produced an identical sensitivity and linear range as that seen using an initial 1 mM concentration.

As mentioned above, edge plane sites are responsible for fast heterogeneous electron transfer kinetics, with polishing of the bppg electrode leading to the formation of significant amounts of edge plane defects meaning that either a polished bppg or an eppg can be used as a sensor for the indirect determination of substituted phenols and phenolic compounds. This is exemplified by the following experiment.

A basal plane pyrolytic graphite electrode was prepared by polishing with alumina lapping compounds, thereby exposing edge plane sites. The polished bppg electrode was placed into a pH 10 buffer solution containing 1 mM PAP with the initial SW-voltammetric response sought, after which additions of phenol were made. Analysis of the peak height versus added phenol concentration produced a linear response ($I_H$=−0.188 [(phenol/M)]+1.74×10$^{-4}$; $R^2$=0.99, N=9) from 50 to 430 μM, which is essentially identical to that observed above using the edge plane pyrolytic graphite electrode. This reiterates the notion that edge plane sites are responsible for the fast electrode kinetics and consequently either a polished bppg or eppg electrode can be used to monitor the voltammetric response.

A control experiment was performed where identical volume sized additions were made of either water or ethanol to a pH 10 buffer solution containing 1 mM PAP without any phenol present. No significant reduction in the PAP voltammetric peak was observed for either the water or the ethanol additions. This indicates that neither dilution effects nor reaction with ethanol were responsible for the decrease in the voltammetric response of the PAP as observed in FIG. 4A. Rather, the latter arises purely from the Gibbs reaction of phenol with QI.

As described earlier, the Gibbs reagent has previously been used spectrophotometrically to detect substituted phenols where it has been observed that the most easily displaced substitutents (good anionic leaving groups) give rise to high yields of dichloroindophenol, while methylphenol and longer alkyl group substitutions, such as hydroxybiphenyl, ethylphenol and hydroxybenzoic acid, gave no detectable coloured product (Josephy et al, supra).

It has been reported that phenol and phenoxyphenol give good yields of coloured products (60 and 63% respectively), methylphenol gives a low yield (18%) while nitrophenol produces no positive result in a Gibbs reaction (Josephy at al, supra). However, this technique is based on spectrophotometric observation of the product of the Gibbs (or related) reaction. In the present invention it is the loss of the benzoquinone monoamine as it reacts with the substituted phenol of choice which is observed. Therefore, in the following Examples, a range of substituted phenols is assessed for use with the method of the invention.

EXAMPLE 2

Detection of 4-phenoxyphenol

Figure 5:
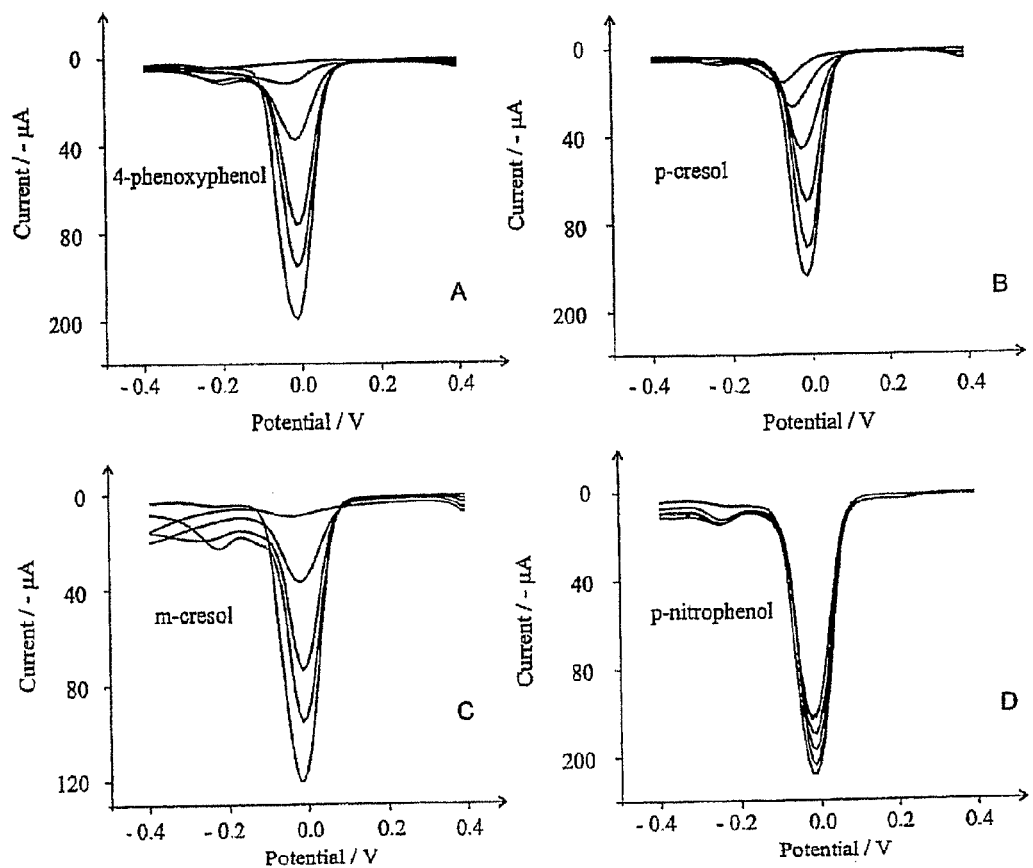
FIG. 5A is a voltammogram showing the response of the addition of 4-phenoxyphenol to a pH 10 buffer solution using an eppg electrode. The 4-phenoxyphenol additions were at concentrations of 50, 100, 150, 200 and 250 μM.
FIG. 5B is a voltammogram showing the response of the addition of p-cresol to a pH 10 buffer solution using an eppg electrode. The p-cresol additions were at concentrations of 100, 200, 300, 400 and 500 μM.
FIG. 5C is a voltammogram showing the response of the addition of m-cresol to a pH 10 buffer solution using an eppg electrode. The m-cresol additions were at concentrations of 99, 196, 291 and 385 µM.
FIG. 5D is a voltammogram showing the response of the addition of p-nitrophenol to a pH 10 buffer solution using an eppg electrode. The p-nitrophenol additions were at concentrations of 100, 200, 300, 400 and 500 µM.

The method of Example 1 was repeated using SWV at an eppg electrode for the detection of 4-phenoxyphenol. The SW-voltammetric responses are shown in FIG. 5A with analysis. Analysis of the peak height versus added 4-phenoxyphenol was found to produce a linear range from 50 µM to 244 µM ($I_H$=−0.51 ([4-phenoxyphenol]/M)+1.2×10$^{-4}$ A; $R^2$=0.98, N=6). The last voltammetric wave, as shown in FIG. 5A has disappeared indicating complete reaction of the 4-phenoxyphenol with the electrochemically generated dichloro-benzoquinone monoamine. In comparison, spectrophotometric methods have reported a 63% yield of dichloroindophenol (Josephy et al, supra). Finally, from the above linear regression data, a limit of detection was found to be 34 µM.

As discussed in section above, the Gibbs reaction requires an optimised pH of 9-10 to facilitate the hydrolysis of the Gibbs reagent to yield dichloro-benzoquinone monoamine (species 2 of Scheme 1) which then undergoes the Gibbs reaction by attacking the substituted phenol. Since the methodology of the present invention does not require such a hydrolysis step the method is considered to able to work at both basic and acidic conditions. This was further explored as described below.

The above method for the indirect detection of 4-phenoxyphenol was repeated using SWV at an eppg electrode at pH 3.4. From analysis of the decreasing peak height versus added phenoxyphenol, two linear ranges were observed. The first was found to occur from 50 µM to 291 µM ($I_H$=−0.15 ([4-phenoxyphenol]/M)+1.6×10$^{-4}$ A; $R^2$=0.99, N=7), while the second was from 130 µM to 264 µM ($I_H$=−0.47 ([4-phenoxyphenol]/M)+2.44×10$^{-4}$ A; $R^2$=0.998, N=6). A similar gradient in comparison to the response obtained in pH 10 buffer is observed suggesting that the method of the invention can be applied in both acidic and basic conditions.

EXAMPLE 3

Detection of p-cresol and m-cresol (methylphenol)

FIGS. 5B and C shows the response of additions of either p-cresol and m-cresol respectively to a 1 mM solution of PAP in pH 10 buffer solution using SW-voltammetry at an eppg electrode. In both cases, analysis of the decreasing wave versus additions of the respective cresol were found to be linear ($I_H$=−0.21 ([p-cresol]/M)+1.08×10$^{-4}$ A; $R^2$=0.9895, N=8) from 99 µM to 431 µM for p-cresol, while m-cresol produced a linear response from 100 µM to 385 µM ($I_H$=−0.29 [(m-cresol/M)]+1.25×10$^{-4}$; $R^2$=0.99, N=8). Note that in all cases, the addition of the substituted phenol of choice is continued until the voltammetric peak stops diminishing indicating that the reaction of the substituted phenol with the electrogenerated dichloro-benzoquinone monoamine has ceased. From the above linear regression data, the limit of detection (3σ) was found to be 32 µM for p-cresol and 30 µM m-cresol.

EXAMPLE 4

Detection of p-nitrophenol

The reaction of p-nitrophenol with the Gibbs reagent has been reported spectrophotometrically not to occur, i.e. no dichloroindophenol was observed using spectrophotometry (Josephy et al, supra). However, as described above, the method of the invention, although taking inspiration from the Gibbs reaction, is different in that it is based on monitoring the loss of the electrogenerated dichloro-benzoquinone monoamine as it reacts with the substituted phenol of choice.

Using the method of the invention, the response of additions of nitrophenol was explored. As depicted in FIG. 5D, the system responds to additions of nitrophenol with a linear response from 50 µM to 385 µM ($I_H$=−0.067 [(p-nitrophenol/M)]+1.29×10$^{-4}$; $R^2$=0.98, N=6), but does not achieve a high sensitivity in comparison to the substituted phenols studied above. This is likely to be due to the presence of the poor $NO_2^-$ leaving group. The limit of detection (3σ) was found to be 40 µM.

In summary, it has been observed that the most easily displaced leaving groups give rise to good sensitivities e.g. (phenoxy) while for poor leaving groups e.g. ($NO_2$) the sensitivity is not so good. Nevertheless, in the latter case, analysis by a method of the invention is still possible in situation where the classical (colorimetric) Gibbs reaction fails.

EXAMPLE 5

Detection of Tetrahydrocannabinol (THC)

Figure 6:
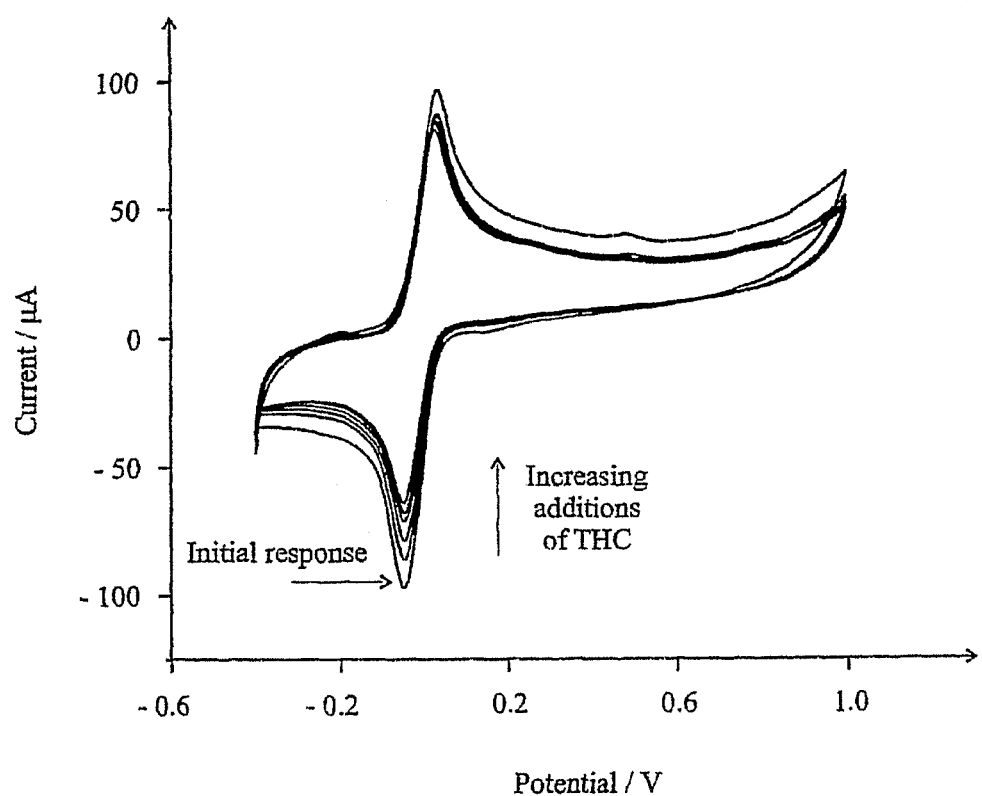
FIG. 6 shows cyclic voltammograms showing the response of tetrahydrocannabinol (THC) additions to a pH 10 buffer solution containing 1 mM PAP using an eppg electrode at a scan rate of 100 mVs$^{-1}$. The THC additions were at concentrations of 100, 196, 291, 385 and 476 µM respectively.

Using cyclic voltammetry, the electrochemical response at an eppg electrode of the electrochemical oxidation of 1 mM PAP in a pH 10 buffer solution was established. Additions of THC were made over the range of 100-476 µM to the solution with the observed response depicted in FIG. 6. As observed for the phenol additions in the preceding Examples, the reduction peak decreased with increasing THC additions, indicating that the protocol works as an indirect methodology for the detection of THC, the active part of *cannabis*. This result was quantified using square wave-voltammetry.

Figure 7:
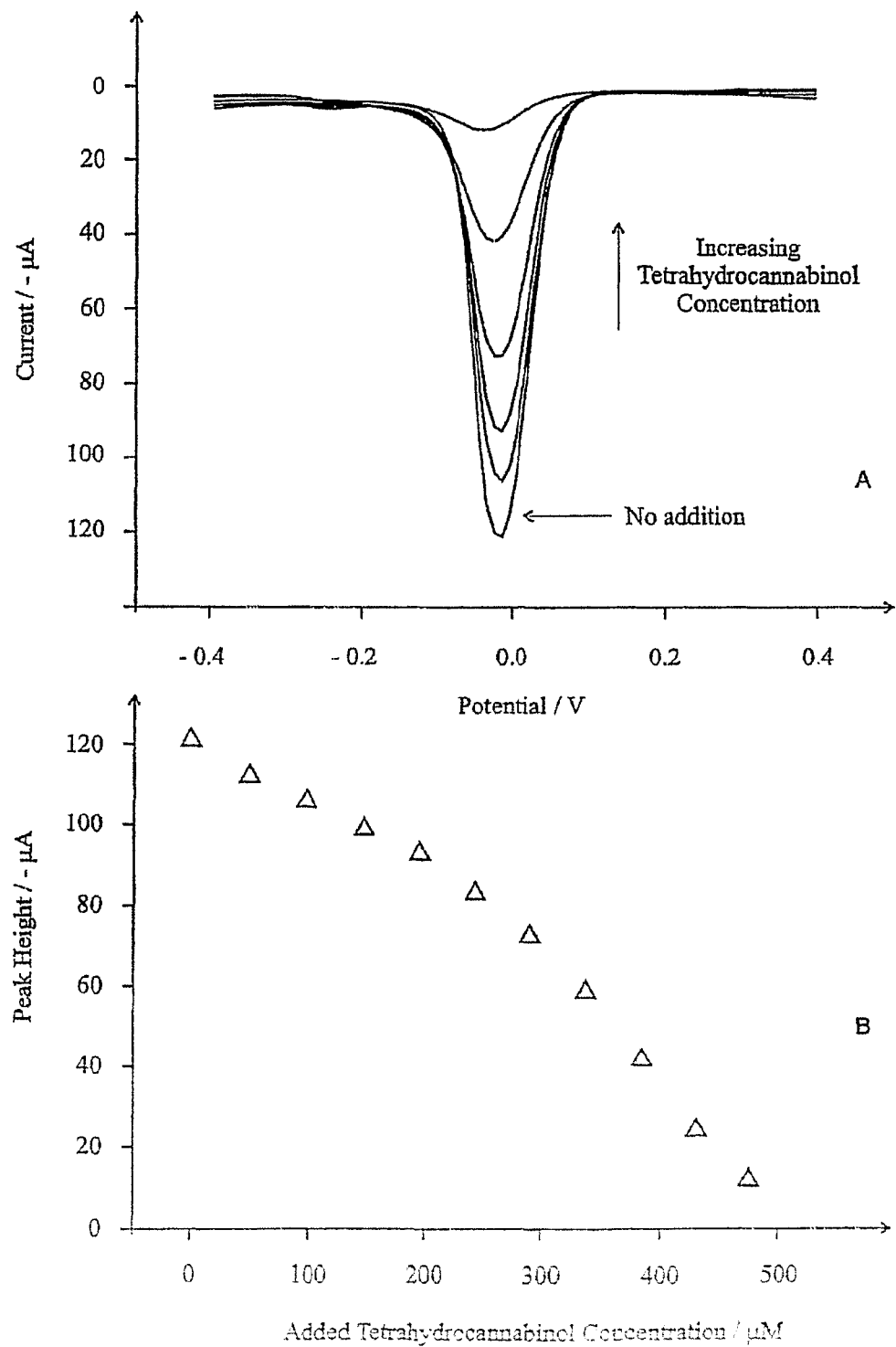
FIG. 7A shows voltammograms of additions of tetrahydrocannabinol (THC) to a solution containing 1 mM 4-amino-2, 6-dichlorophenol in pH 10 buffer using an eppg electrode. The square wave parameters were: −0.4V (vs standard calomel electrode) for 10 seconds followed by a potential sweep from +0.4V to −0.4V. The additions of THC were at concentrations of 99, 196, 291, 385 and 476 µM respectively.
FIG. 7B is a graph of the peak height versus added THC concentration for voltammogram of FIG. 7A.

Using a 1 mM solution containing 4-amino-2,6-dichlorophenol in a pH 10 buffer solution, the initial SW voltammetric response was obtained using an edge plane pyrolytic graphite electrode. The response of additions of tetrahydrocannabinol was explored. As depicted in FIG. 7A, the voltammetric peak was found to decrease with increasing additions of THC. Analysis of the peak height versus added THC concentrations revealed two linear parts of the calibration curve (FIG. 7B). The first part was linear from 50 to 245 µM ($I_H$=−0.148 [(THC/M)]+1.21×10$^{-4}$; $R^2$=0.994, N=6) with the second from 290 to 476 M ($I_H$=−0.337 [(THC/M)]+1.71× 10$^{-4}$; $R^2$=0.997, N=5). From this, the limit of detection (3σ) was found to be 25 µM.

EXAMPLE 6

Detection of EGCG and EGC at an Eppg Electrode

Figure 8:
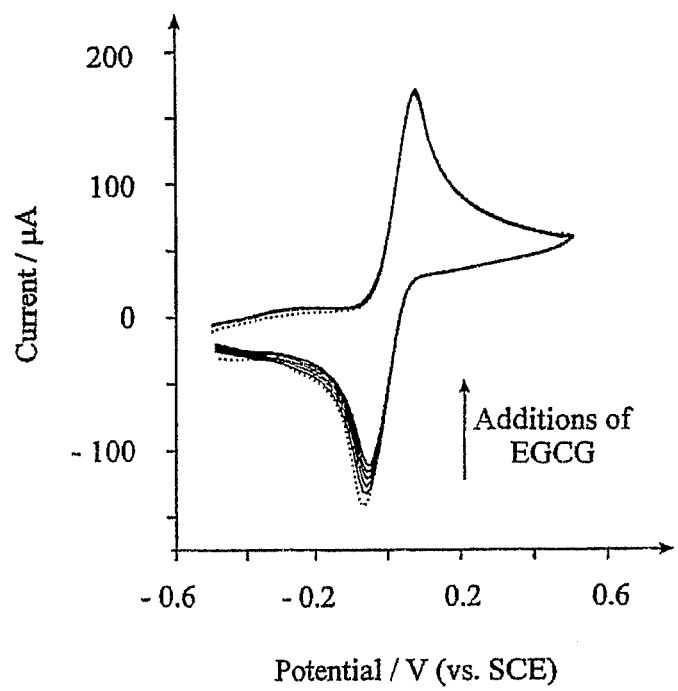
FIG. 8 shows cyclic voltammetric responses due to the additions of EGCG to a pH 10 buffer solution using an edge plane pyrolytic graphite electrode. All scans were recorded at 100 mVs$^{-1}$. The dotted scan is the initial response in the absence of any EGCG. Additions of EGCG were at 1, 2, 3, 4 and 5 mM.
Figure 9:
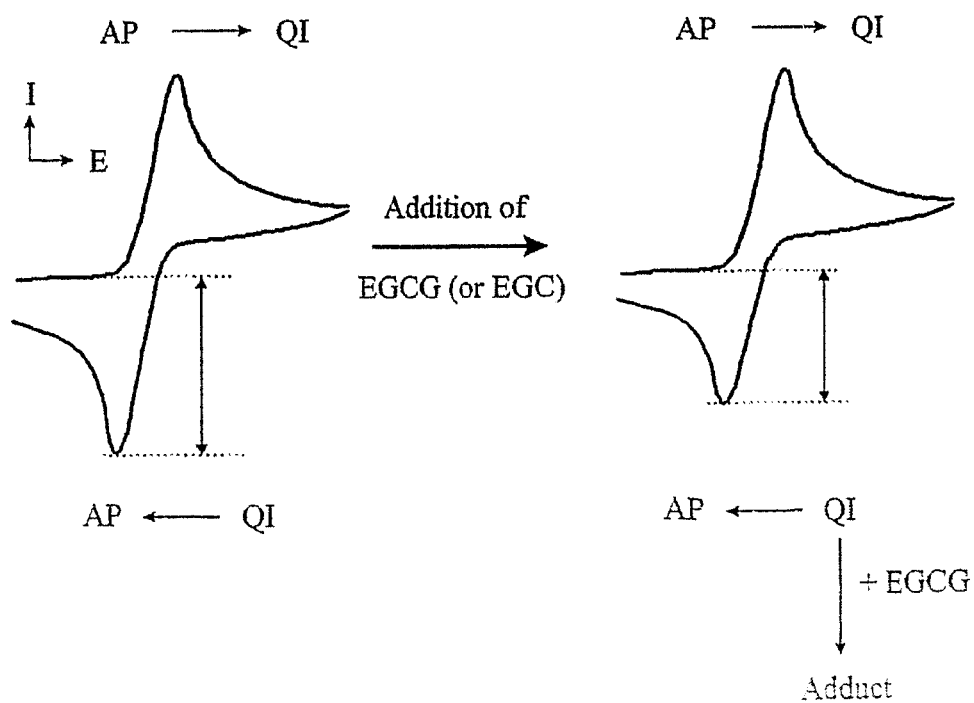
FIG. 9 shows an electrochemical sensing protocol in which the reduction in magnitude of the reverse peak from the addition of EGCG or EGC provides the analytical signal.

A 1 mM solution containing 2,6-dichloro-p-aminophenol (AP) in a pH 10 buffer was first prepared and examined with cyclic voltammetry at an eppg electrode. The voltammetric response is depicted in FIG. 8 (dotted line) which exhibits an oxidation and reduction with peak potentials at ca.+0.08 V and ca.−0.07 V (vs. SCE) respectively, which are due to the redox couple of the aminophenol-quinoneimine (PAP-QI) system. A peak-to-peak separation of 150 mV was observed (at 100 mVs$^{-1}$), indicating quasi-reversible electrode kinetics. 1 mM additions of EGCG were then made to the buffer solution, which, as observed in FIG. 8, results in the reduction peak of voltammetric profile to decrease. This reduction in the size of the voltammetric peak is due to the loss of the quinoneimine (QI), which reacts with EGCG to form an adduct (see FIG. 9).

EXAMPLE 7

Detection of EGCG and EGC at a Modified Bppg Electrode

Bppg electrodes were modified with 2,6-diphenyl-4-amino-phenol ("diphenyl-AP") and subsequently used to detect EGCG and EGC. Diphenyl-AP has the same required electrochemical functionalities as other PAPs but has two diphenyl groups so greatly reducing the compound's solubility in aqueous solutions. The diphenyl-AP compound was immobilised onto the electrode surface by taking a freshly prepared bppg electrode and immersing into a solution of 1 mM diphenyl-AP in acetonitrile for five minutes after which the electrode was taken out and gently washed with distilled water. Typically, the peak current after stabilisation was found to be an average of 25 (±10) μA which likely reflects the variation in surface roughness of the bppg electrode each time the electrode is prepared.

The modified bppg electrode was placed into a pH 10 buffer solution where, using square wave voltammetry, the potential was held at +0.2 V (vs. SCE) for 5 seconds, followed by sweeping the potential from +0.2 V to −0.4 V (vs. SCE). Square wave voltammetry was chosen since it provides an easy way to monitor the loss of the voltammetry peak on additions of the catechin compounds. A large reduction wave having a peak maximum at ca.−0.11 V (vs. SCE) was initially observed. The square wave protocol was continuously repeated to assess the stability of the voltammetric peak. It was found that 12 cycles were usually needed to stabilise the peak, which was found to typically decrease by ca. 30% of its initial value. The 12 cycles indicate that the modified electrode needs a pre-treatment to be applied which need last not longer than 60 seconds at +0.2 V (vs. SCE).

Figure 10:
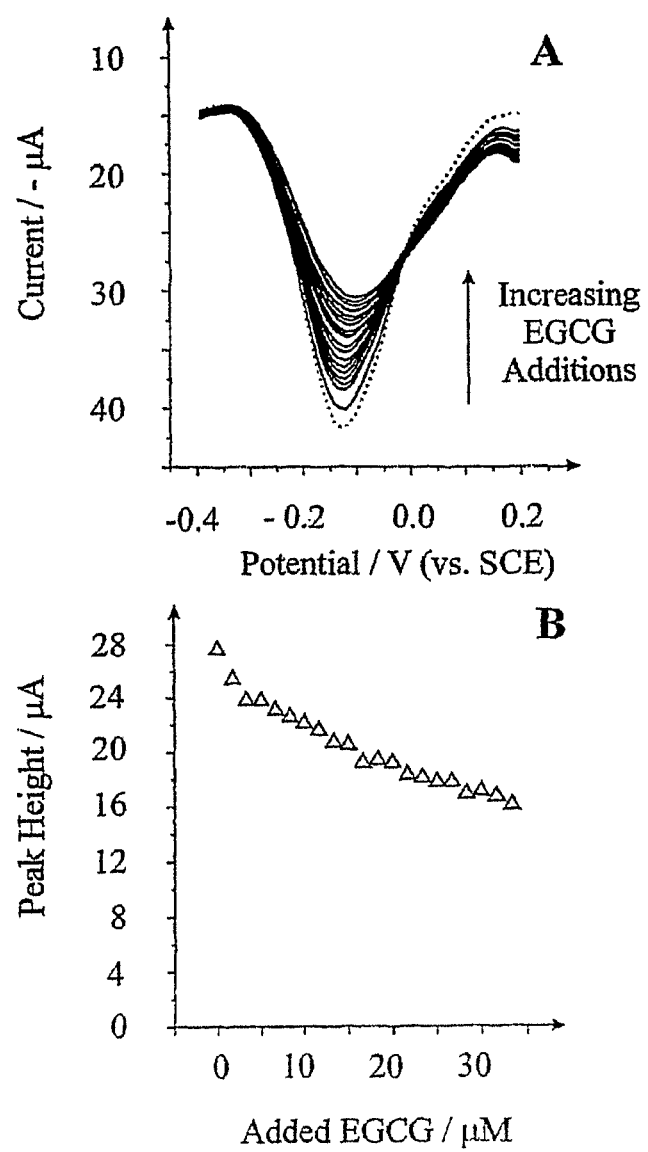
FIG. 10A shows the square-wave voltammetric response using a bppg electrode modified with 4-amino-2,6-diphenylphenol in a pH 10 buffer solution to additions of 1.7 µM EGCG. The square-wave parameters were: +0.2 V for 5 seconds followed by potential sweep from +0.2 to −0.4 V (vs. SCE)
FIG. 10B shows the analysis of the observed peak height (from FIG. 10A) versus added EGCG concentration.

The response of the diphenyl-AP modified bppg electrode toward EGCG additions in a pH 10 buffer solution was next investigated. FIG. 10 shows the response of 1.7 μM additions of EGCG where analysis of the peak height ($I_H$) versus added EGCG concentration, as shown in FIG. 10B produces substantially linear range from 3 μM to 32 μM with the following linear regression: $I_H/A = −0.29\ [(EGCG/M)] + 2.5 \times 10^{-5}$ A; $R^2 = 0.98$; N=19. The potential range was well resolved from that of the direct electrochemical oxidation of EGCG (which occurs at ca.+0.72 V vs. Ag/AgCl; see Kumamoto et al, Anal. Sci. 16, 2000, 139), thus removing any possibility of electrode fouling caused by direct oxidation.

Figure 11:
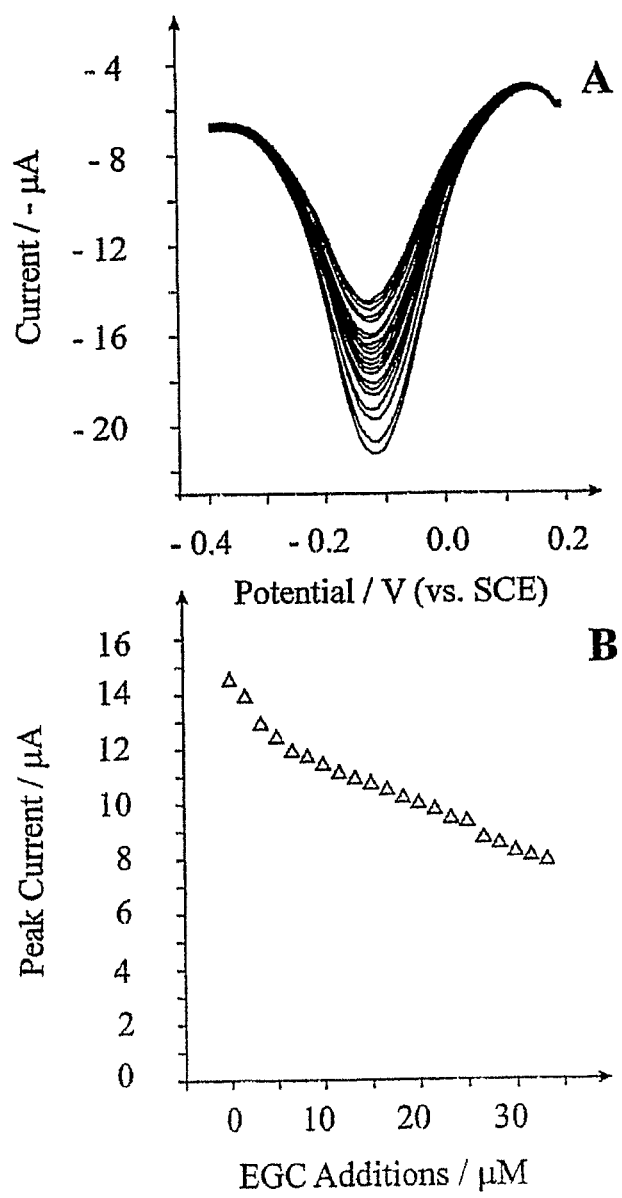
FIG. 11A shows the response of 1.7 µM additions of EGC into a pH 10 buffer solution using a bppg electrode modified with 4-amino-2,6-diphenylphenol. The modification procedure and square-wave parameters are the same as for FIG. 10.
FIG. 11B shows the analysis of the observed peak height versus added EGC concentration.

The response of 1.7 μM additions of EGC into a pH 10 buffer solution using the diphenyl-AP modified bppg electrode was then explored. FIG. 11A shows the square-wave voltammetric profiles, which clearly diminish as EGC is added into the solution. Analysis of the peak height versus added EGC concentration is depicted in FIG. 11B, where two linear ranges are observed; the first from 1.7 μM to 10 μM ($I_H/A = −2.7\ [(EGC/M)] + 6.9 \times 10^{-5}$ A; $R^2 = 0.98$; N=6) and the second from 10 μM to 32 μM ($I_H/A = −0.9\ [(EGC/M)] + 5.1 \times 10^{-5}$ A; $R^2 = 0.99$; N=8). The modified bppg electrode was explored with additions made over the range 0.8 μM to 8.3 μM from a solution consisting of both EGCG and EGC at the same concentration which produced the following linear regression: $I_H/A = −0.85\ [(EGCG+EGC/M)] + 3.2 \times 10^{-5}$ A; $R^2 = 0.97$; N=10. Comparison of this linear regression with that obtained from the additions of EGCG and EGC reveal an identical response.

The above experiments demonstrate that the diphenyl-AP-modified bppg electrode was successful in detecting the anti-carcinogenic catechin compounds EGCG and EGC, obviating the need to add the aminophenol into the solution. The modification of the electrode avoids the need to dissolve the aminophenol compound into the solution phase. For example, this methodology could be utilised in end of column detectors thus obviating the need to dissolve the electrochemical marker into the carrier solution.

EXAMPLE 8

Detection of EGCG and EGC in Green Tea

EGCG and EGC were detected in a sample of green tea. A 1.97 g sample of green tea (Xiamen Tea IMP, & EXP. CO., LTD) was placed into 100 mL of boiling distilled water, constantly stirred and held at a rolling boil for 40 minutes to allow the tea to infuse. The tea infusion was allowed to cool and was consequently filtered. This solution was then diluted 1:1 with pH 10 buffer.

Figure 12:
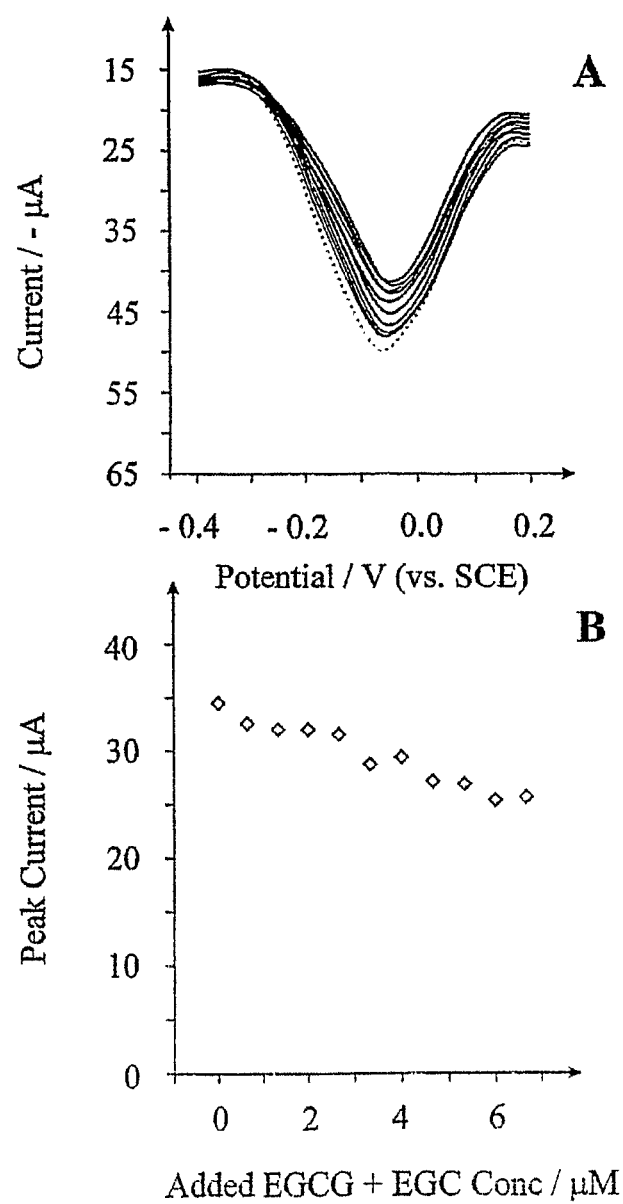
FIG. 12A shows typical square-wave voltammetric responses using a bppg electrode modified with 4-amino-2, 6-diphenylphenol from analysis of a green tea sample, with 0.7 µM additions of EGCG and EGC made to the solution. The square-wave parameters were: +0.2 V for 5 seconds followed by potential sweep from +0.2 to −0.4 V (vs. SCE)
FIG. 12B shows the analysis of the observed peak height (from FIG. 12A) versus added EGCG/EGC concentration.

A phenyl-AP modified bppg electrode was prepared (see Example 7) and placed into the tea sample. Using square-wave voltammetry, the electrochemical response of additions of 0.7 μM EGCG and EGC (made up in the same solution) was explored. Typical square-wave voltammograms are depicted in FIG. 12, where the additions of EGCG and EGC made to the green tea sample results in a decrease in the voltammetric profile. A standard addition plot of peak height versus added EGCG and EGC concentration is shown in FIG. 12B. Analysis using the standard addition protocol reveals that 180 (±5) mg of EGCG and EGC exists in 1 g of green tea. This content of catechins is in the same order of magnitude as that reported by Pelillo et al above, who explored five green tea samples with HPLC coupled with UV and MS-electrospray detection. They found that the total amount of catechins varied from 90 mg/g to 760 mg/g depending on the source of the green tea and where the total amount of EGCG and EGC were found to vary between 26 to 412 mg/g and 12 to 100 mg/g respectively in the green tea sample.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

The invention claimed is:
1. A method of detecting a phenol in a sample, comprising:
   (a) oxidising a first compound at a working electrode of an electrochemical sensor to form a second compound which is operatively reactive with the phenol;
   (b) contacting the phenol with the second compound in the presence of an electrolyte, such that the second compound reacts with the phenol; and

(c) determining an electrochemical response of the working electrode to the consumption of the second compound on reaction with the phenol;
wherein the first compound in step (a) is a 4-aminophenol, and wherein the second compound reacts to covalently bind the phenol in step (b).

2. A method according to claim 1, wherein the first compound is a compound of the formula (I):

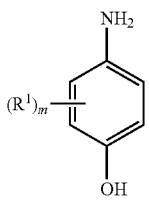

(I)

wherein
m is 0, 1, 2, 3 or 4;
each $R^1$ is independently $R^2$, or is hydrocarbyl or heterocyclyl, either of which is optionally substituted with 1, 2, 3, 4 or 5 $R^2$;
each $R^2$ is independently selected from halogen, trifluoromethyl, cyano, nitro, oxo, $=NR^3$, $R^3$, $-OR^3$, $-C(O)R^3$, $-C(O)OR^3$, $-OC(O)R^3$, $-N(R^3)R^4$, $-C(O)N(R^3)R^4$, $-S(O)_lR^3$ and $-C(R^3)_3$;
$R^3$ and $R^4$ are each independently hydrogen, or are selected from $C_{1-6}$ alkyl, $-(CH_2)_k$-carbocyclyl and $-(CH_2)_k$-heterocyclyl, any of which is optionally substituted with 1, 2, 3, 4 or 5 substituents independently selected from halogen, hydroxy and $C_{1-6}$ alkyl; and
l is 0, 1 or 2;
and wherein the first compound is oxidised at the working electrode to form a second compound which is of the formula (II):

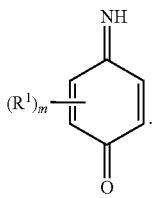

(II)

3. The method according to claim 2, wherein m is 0, 1 or 2.

4. The method according to claim 2, wherein the or each $R^1$ is independently selected from $-NR^3R^4$, halogen, $C_1$, $C_2$, $C_3$ or $C_4$ alkyl, $C_1$, $C_2$, $C_3$ or $C_4$ haloalkyl, $C_1$, $C_2$, $C_3$ or $C_4$ alkoxy, and $C_2$, $C_3$ or $C_4$ alkenyl, and wherein $R^3$ and $R^4$ are each independently selected from hydrogen, $-OH$, $C_1$, $C_2$, $C_3$ or $C_4$ alkyl, $C_1$, $C_2$, $C_3$ or $C_4$ haloalkyl, $C_1$, $C_2$, $C_3$ or $C_4$ alkoxy, and $C_2$, $C_3$ or $C_4$ alkenyl.

5. The method according to claim 4, wherein the or each $R^1$ is halogen.

6. The method according to claim 5, wherein the first compound is of the formula (IA):

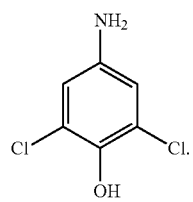

(IA)

7. The method according to claim 2, wherein the or each $R^1$ is aryl.

8. The method according to claim 7, wherein the first compound is of the formula (IB):

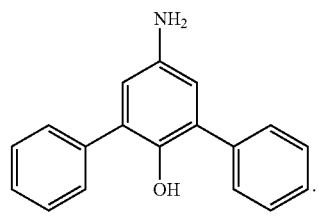

(IB)

9. The method according to claim 1, wherein the working electrode is a screen printed electrode, a metallic electrode, an edge plane pyrolytic graphite electrode, a basal plane pyrolytic graphite electrode, a glassy carbon electrode, a boron doped diamond electrode or a highly ordered pyrolytic graphite electrode.

10. The method according to claim 1, wherein determination of the electrochemical response comprises measuring the current flow between the working electrode and a counter electrode to determine the amount of the phenol.

11. The method according to claim 10, wherein the working electrode is maintained at a constant voltage.

12. The method according to claim 10, wherein said current is measured using linear sweep or cyclic voltammetry, square wave voltammetry, or a pulsed voltammetry technique.

13. The method according to claim 1, wherein the phenol is a para-substituted phenol.

14. The method according to claim 1, wherein the phenol is phenol, 4-phenoxyphenol, p-methylphenol, m-methylphenol, nitrophenol or tetrahydrocannabinol.

15. The method according to claim 1, wherein the phenol is a component or a metabolite of cannabis.

16. The method according to claim 1, wherein the phenol is a natural or synthetic cannabinoid or a metabolite thereof.

17. The method according to claim 15, wherein the phenol is a cannabis metabolite found in urine.

18. The method according to claim 15, wherein the phenol is 11-nor-9-carboxy-9-tetrahydrocannabinol.

19. The method according to claim 1, wherein the phenol is a catechin.

20. The method according to claim 19, wherein the phenol is (−)-epigallocatechin gallate (EGCG) or (−)-epigallocatechin (ECG).

21. The method according to claim 1, wherein the electrolyte comprises said first compound.

22. The method according to claim 1, wherein the working electrode comprises said first compound.

* * * * *